United States Patent [19]
Kolz et al.

[11] Patent Number: 5,916,170
[45] Date of Patent: Jun. 29, 1999

[54] METHOD AND APPARATUS FOR CURVATURE DETECTION IN VESSELS FROM PHASE SHIFTS OF A PLURALITY OF INPUT ELECTRICAL SIGNALS

[75] Inventors: Matthew L. Kolz, Stanford; Peter J. Fitzgerald, Menlo Park; Gordon S. Kino, Stanford, all of Calif.

[73] Assignee: The Board of Trustees of the Leland Stanford Junior University, Stanford, Calif.

[21] Appl. No.: 09/158,969

[22] Filed: Sep. 21, 1998

Related U.S. Application Data

[60] Provisional application No. 60/059,855, Sep. 24, 1997.
[51] Int. Cl.⁶ ....................................................... A61B 8/00
[52] U.S. Cl. ......................... 600/462; 600/466; 600/467
[58] Field of Search .................................. 600/437, 459, 600/462, 466, 467

[56] References Cited

U.S. PATENT DOCUMENTS

| | | | |
|---|---|---|---|
| 4,794,931 | 1/1989 | Yock | 128/660.03 |
| 4,917,097 | 4/1990 | Proudian et al. | 128/662.06 |
| 5,000,185 | 3/1991 | Yock | 128/662.03 |
| 5,076,278 | 12/1991 | Vilomerson et al. | 128/662.03 |
| 5,186,177 | 2/1993 | O'Donnell et al. | 128/662.06 |
| 5,453,575 | 9/1995 | O'Donnell et al. | 600/462 |

OTHER PUBLICATIONS

Schwarzacher, S., Impact of curve distortion errors on intravascular ultrasound measurements and three–dimensional reconstructions, Am. J. Cardiology, vol. 79, pp. 384–387, 1997.

Prati, F., Usefulness of on–line three–dimensional reconstruction of intracoronary ultrasound for guidance of stent deployment, Am. J. Cardiology, vol. 77, pp. 455–461, 1996.

Klein, H., 3D surface reconstruction of intravascular ultrasound images using personal computer hardware and a motorized catheter control, Cardiovasc Intervent Radiol, vol. 15, pp. 97–101, 1992.

Rosenfield, K., Three–dimensional recontruction of human coronary and peripheral arteries from images recorded during two–dimensional intravascular ultrasound examinations Circulation, vol. 84, No. 5, pp. 1938–1956, 1991.

*Primary Examiner*—Marvin M. Lateef
*Assistant Examiner*—Ali M. Imam
*Attorney, Agent, or Firm*—Lumen Intellectual Property Service

[57] ABSTRACT

An ultrasound imaging apparatus for measuring the curvature of a vessel consisting of a distal transducer mounted on a transducer supporting device. A resilient deformable material is attached to the transducer supporting device and allows the angular orientation of the transducer to change based on the local vessel curvature. The ultrasound imaging apparatus emits ultrasound radiation from multiple pulsed electronic signals as the apparatus is moved through a vessel or sheath catheter at a known velocity. The distal transducer receives the scattered ultrasound radiation and differences in the phase shifts of the scattered ultrasound radiation are analyzed to detect or measure curvature.

19 Claims, 7 Drawing Sheets

METHOD AND APPARATUS FOR CURVATURE DETECTION IN VESSELS FROM PHASE SHIFTS OF A PLURALITY OF INPUT ELECTRICAL SIGNALS

RELATED APPLICATIONS

This application claims priority from U.S. provisional application 60/059,855 filed Sep. 24, 1997, which is herein incorporated by reference.

FIELD OF THE INVENTION

This invention relates generally to an apparatus and method for detecting and measuring curvature in vessels using ultrasound. More particularly, it relates to an ultrasound imaging catheter apparatus with a distally mounted transducer for measuring intravascular curvature and method for doing the same.

BACKGROUND ART

Catheter based technology continues to grow rapidly as new innovative methods are developed to examine and treat areas once inaccessible without more invasive procedures. Much of the original motivation for this technology was to provide intravascular and cardiac catheters that could be used for cardiac diagnosis and interventions. Many specialized ones have been developed and are commercially available, and, as the technology has matured, these catheters have found more widespread use to areas of the body outside the thorax including the cranium and peripheral anatomy. Also, the catheters are not limited to blood vessels but may be used in other passages within the body.

Single function diagnostic catheters are now available to measure blood pressure, quantify blood velocity, and inject contrast dyes. More advanced diagnostic catheters image the internal physiology by optical or acoustical means. Specialized interventional catheters are in common use in catheterization laboratories today and perform procedures such as angioplasty, atherectomy, and stent placement. The most widely utilized catheter based method of imaging vessels is intravascular ultrasound (IVUS). Using ultrasound and a distally mounted transducer to generate echographic images during catherization procedures has a number of advantages over angiography. Furthermore, the location of the distal region or the catheter can be accurately determined using transducers of particular geometries; for example see Vilkomerson et al. U.S. Pat. No. 5,259,837.

Principles of IVUS involve using a sheath-catheter that is inserted into the vessel to be imaged. An intraluminal imaging catheter with at least one distally mounted ultrasound transducer is inserted into the sheath catheter. Generally there is either an array of stationary transducers (for examples see U.S. Pat. No. 9,417097 to Prodian et al. and U.S. Pat. No. 5,186,177 to O'Donell et al.) or a rotating transducer mounted at the distal end of the imaging catheter (U.S. Pat. Nos. 4,794,931 and 5,000,185 to Yock) to obtain full radial 2-dimensional images of the vessel. The intraluminal catheter is translated through the sheath catheter as 2-dimensional images are acquired. The images can be stacked to obtain a 3-dimensional image of the vessel under study.

The methods above assume that the imaged vessel has a linear shape introducing significant error into the constructed 3-dimensional images when the vessel imaged has curvature. In many catheterization procedures, it is highly desirable to have accurate, complete visualization of the total shape of the vessel or passage of interest including the longitudinal morphology or the curvature of the vessel. IVUS techniques described in the prior art that attempt to include vessel curvature use receiver transducers that are generally external to the body of the patient to receive the signals generated from the transducer or transducers of the intraluminal imaging catheter.

Difficulties associated with current IVUS techniques have been recognized and reported in several studies that attempt to do three-dimensional vessel reconstruction in tortuous vessel; see Prati et. al "Usefulness of On-line Three-dimensional Reconstruction of Intracoronary Ultrasound for Guidance of Stent Deployment", Am. J. Cardiol., Vol. 77, pp. 455–461, Mar. 1, 1996; Rosenfield et. al "Three-dimensional Reconstruction of Human Coronary and Peripheral Arteries from Images Recorded During Two-dimensional Intravascular Ultrasound Examination", Circulation, Vol. 85, pp. 1938–1956, November 1991; and Schwarzacher et. al "Impact of Curve Distortion Errors on Intravascular Ultrasound Measurements and Three-dimensional; Reconstruction" Am. J. Cardiol., Vol. 79, pp. 384–387, Feb. 1, 1997.

Another study examined the possibility of utilizing biplane angiography (fluoroscopy) to record vessel curvature while IVUS imaging was performed to visualize the vessel tissues; see Hans-Martin et. al "3D-surface reconstruction of intravascular ultrasound images using personal computer hardware and a motorized catheter control" Cardidovasc. Intervent. Radiol. Vol. 15, pp. 97–101, 1992. However, the method described is difficult to implement and subject to errors due the inability to precisely locate distal transducer region of the catheter within the vessel. Additionally, the use of angiography is difficult to interface with the current software and external hardware used in an ultrasound laboratory.

What is needed is an apparatus and method for detecting or measuring the curvature of vessels. The measuring device should not require additional external transducer receiver devices or additional external radiation sources. Additionally, the imaging apparatus should use ultrasound technology so that the imaging apparatus can be attached to existing ultrasound equipment. The apparatus should be simple so that it may miniaturized for imaging small vessel in the human body.

OBJECTS AND ADVANTAGES

Accordingly, it is a primary object of the present invention to provide an apparatus and method for determining the curvature of a vessel. The apparatus contains both an ultrasound source and the receiving source, thus, eliminating the need additional receivers or radiation sources outside of the cavity or vessel. The apparatus is based on ultrasound techniques and is easily adapted to existing ultrasound computer imaging systems. The apparatus and method of this invention are not limited to applications in IVUS but can also be applied to measuring the curvature of vessels that are otherwise inaccessible. The new method for measuring curvature of a vessel can be also be used to correct 3-dimensional images obtained by standard IVUS techniques.

SUMMARY

The objects and advantages are met by using an apparatus with an ultrasound transmitting and receiving transducer or transducers to detect the phase shifts in the electrically generated, pulsed, acoustical signals scattered from within the vessel.

The word vessel is generically used to describe a tube or a duct that the apparatus or catheter apparatus is inserted into to measure its curvature. Besides being an artery in a human body, vessel can also be passages in experimental animals or even non-biological passages such as plumbing. In biological settings a catheter apparatus is used and the surroundings of the intraluminal catheter imaging catheter will typically consist of tissue, fluid, and the sheath catheter. In non-biological settings, the apparatus is not necessarily a catheter apparatus and will measure the curvature of the vessel if the surroundings of the vessel allow acoustic penetration or reflection.

The apparatus consists of an ultrasound transducer that is mounted on a transducer supporting device preferably at an angle relative to the tangent of the vessel walls or tangent of the sheath catheter's center line. The transducer supporting device and ultrasound transducer is moved in or out of the vessel at a known velocity by a drive shaft or a cable. Alternatively, the transducer supporting device is motorized. A signal station is electrically connected to the transducer and is used for generating pulsed output electrical signals to the ultrasound traducer while the transducer and transducer supporting device move through the vessel. The transducer operates in an output mode and converts the generated pulsed output electrical signals from the signal station into ultrasound radiation. The ultrasound radiation interacts with the vessel material and is scattered. The scattered ultrasound radiation is received by the transducer that also operates in a receiving mode, whereby the received scattered ultrasound radiation is converted into input electrical signals. The input electrical signals are transmitted through the electrical connection from the ultrasound transducer to the signal station for processing. The phases of consecutively processed input signals are compared for changes that indicate curvature in the vessel.

For biological settings, an ultrasound apparatus is a catheter device constructed from a sheath catheter and intraluminal imaging catheter with a distally mounted ultrasound transducer. The ultrasound transducer is mounted on a transducer supporting device at an angle relative to the tangent of the sheath catheter's walls or center-line. The transducer supporting device and transducer are moved back or forth through the sheath catheter at a known velocity by a cable or a drive shaft. A signal station, that is electrically connected to the transducer, is used for generating pulsed output electrical signals while the intraluminal imaging catheter is moving through the sheath catheter. The distally mounted catheter operates in an output mode and converts the pulsed output electrical signals from the signal station into ultrasound radiation. The ultrasound radiation interacts with the vessel material and the sheath catheter and is scattered. The scattered ultrasound radiation is received by the transducer that also operates in a receiving mode, whereby the received ultrasound radiation is converted into input electrical signals. The input electrical signals are transmitted through an electrical connection to the signal station for processing. The phases of consecutively processes signals are compared for changes in phases shifts that indicate curvature in the vessel.

A catheter apparatus is also described that further includes a resilient deformable material connected to a transducer supporting device. The resilient deformable material provides a region of mobility between the transducer support device and the sheath catheter. The resilient deformable material can be any material that is pressure responsive and returns to its original form after compression. For example the resilient deformable material can be rubber, foam, a leaf spring, or combinations thereof. The resilient deformable material serves the purpose of allowing the transducer supporting device and the transducer to change angular orientation relative to the tangent of the vessel wall or sheath catheter's center line, whereby the angular orientations are dependent on the local curvature. An analysis of phase shifts of the input signals described above will further allow for the curvature of the vessel to be measured and quantified.

DETAILED DESCRIPTION

Figure 1:
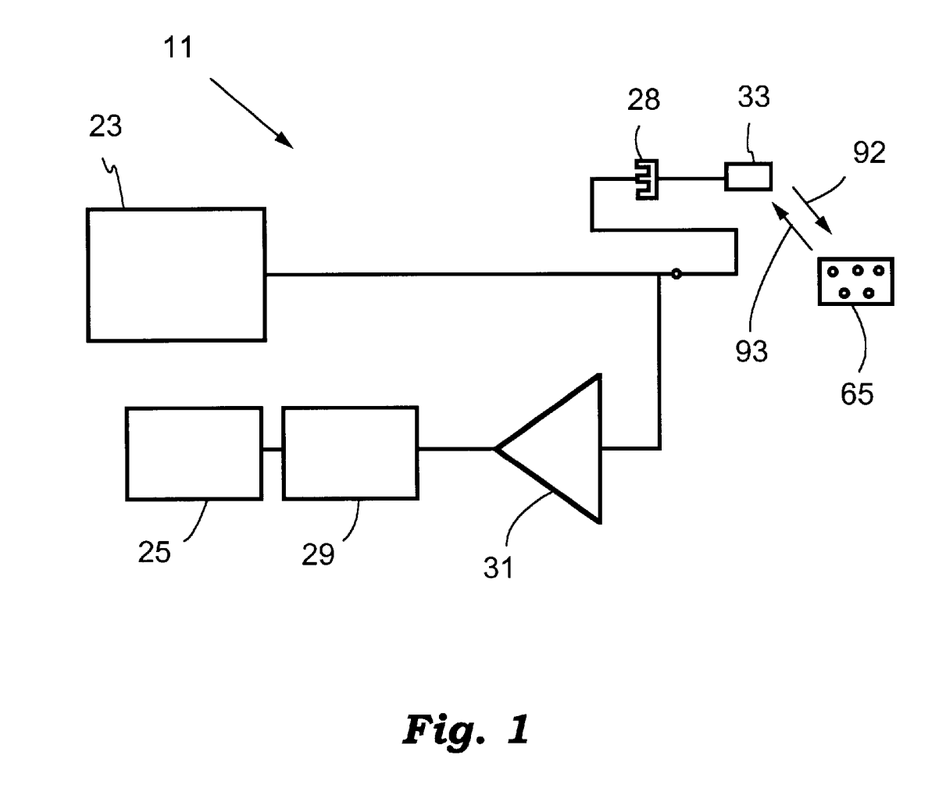
FIG. 1 is a block diagram of the catheter based pulsed wave system as utilized in standard IVUS techniques and with the ultrasound apparatus of this invention.

FIG. 1 is a simplified block diagram of a signal station 11. The signal station has a pulse generator 23 for sending electrical signals to a transducer 33. The electrical pulses are converted to ultrasound radiation by a transducer 33 and the ultrasound radiation is scatted by the material 65. The scattered radiation is received by transducer 33. The transducer 33 converts the scattered ultrasound radiation into electrical signals and the electrical signals are sent to a signal processor 25 through an amplifier 31 and a filter 29.

The ultrasound apparatus is connected to a signal station 11 by any electrical contact that is suitable for the equipment. FIG. 1 illustrates a plug 28 that establishes an electrical connection between the ultrasound apparatus the signal station 11. A preferred embodiment of the ultrasound apparatus includes an ultrasound transducer 33 that is distally mounted to an ultrasound catheter apparatus and is used for measuring the curvature of small vessels. The ultrasound transducer 33 is both an ultrasound radiation source and an ultrasound detector and, therefore, the apparatus requires only a single transducer to be operative.

Again referring to FIG. 1, an electrical signal, in the form of a pulse, is sent from the generator 23 to the transducer 33 and is converted to ultrasound radiation at a fixed pulse repetition frequency, $f_{prf}$, or repetition period, $T_{prf}$. The acoustic wave-form 92 travels at a velocity, c, away from the transducer and is partially reflected by each of the many scatterers 65 encountered by the ultrasound beam 92. If the transmitted pulse shape is given by $s_T(t)$, and the ith scatterer is at a distance, $d_i$, from the transducer, the received ultrasound signal 93, $s_{R1}(t)$, will be the sum of the signals from each of the I scatterers and may be modeled as:

$$s_{RI}(t) = \sum_{i=1}^{I} s_T\left(t - \frac{2d_i}{c}\right)$$

If there is relative motion between the transducer 33 and the scatterers 65, the signals received from the subsequent pulses will be different. If the relative velocity in the direction parallel to the beam is constant and equal to $v_{\parallel}$ the received signal one pulse repetition period, $T_{prf}$, after $S_{R1}(t)$ will be:

$$s_{R2}(t) = \sum_{i=1}^{I} A_i s_T\left(t - \frac{2(d_i + v_{\parallel}T_{prf})}{c}\right)$$

where each of the scatterers 65 is now at a depth differing from the original by $v_{\parallel}T_{prf}$. The term preceding the transmitted pulse, $A_i$, is unique for each scatterer and is a complicated function of the beam pattern, attenuation, and velocity perpendicular to the beam. Motion of the scatters 65 will not be a major source of error when the pulse repetition frequency is high. Thus by processing a series of received wave-forms, it is possible to derive $v_{s1}$. If the transmitted electrical pulses, $s_T$, have a carrier frequency $f_c$, the phase shift due to the time shift of $$\frac{2(v_{\parallel}T_{prf})}{c} \text{ will be } 2\pi f_c \frac{2(v_{\parallel}T_{prf})}{c}.$$

In this case, the phase shift and time shift represent a means to derive the velocity parallel to the beam, $v_{\parallel}$.

Figure 2A:
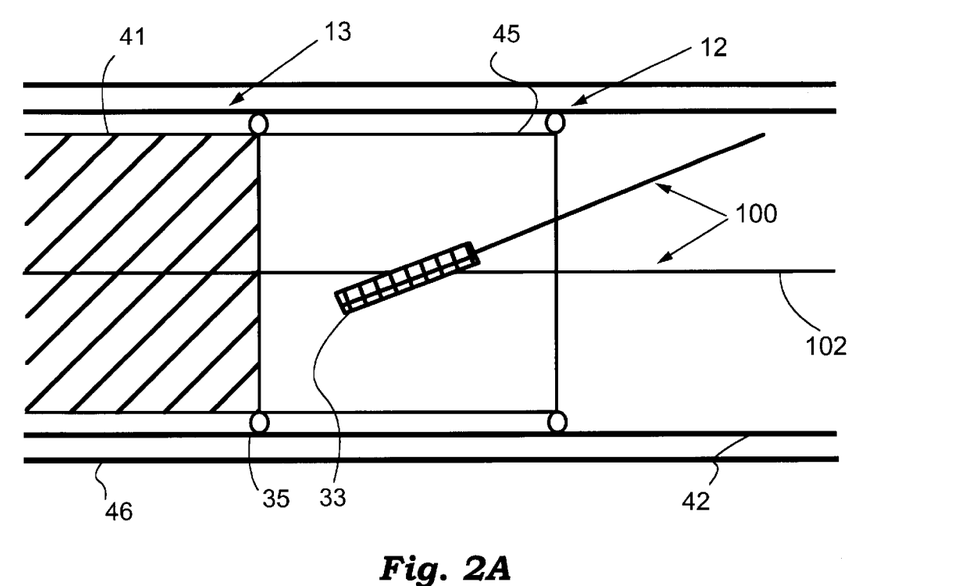
FIGS. 2A–2B are longitudinal cross sectional views of an ultrasound catheter apparatus illustrating the change in the angle of a transducer relative to the tangent of the catheter's centerline in a vessel with curvature versus a straight vessel.

FIG. 2A shows two-dimensional longitudinal cross section of an ultrasound imaging catheter apparatus 12 in straight vessel 46. The ultrasound imaging apparatus 12 consists of a sheath catheter 42 and a flexible intraluminal ultrasound catheter 13. The flexible intraluminal ultrasound catheter 13 comprises of a transducer 33, a transducer support device 45, and a flexible cable 41. The ultrasound transducer 33 is mounted on the transducer support device 45 and is connected to the flexible cable 41. The flexible cable 41 is used to translate the transducer supporting device 45 and transducer 33 through the sheath catheter 42 at a known velocity. The flexible cable 41 is attached to a translation device (not shown) that controls the position of the transducer within the sheath catheter 42. The angular orientation 100 of the transducer 33 is α degrees with respect to the tangent 102 of the catheter's centerline.

A resilient deformable material 35 is connected to the transducer supporting device 45 and provides a region of mobility between the transducer support device 45 and the sheath catheter 42 such that the angular orientation of the transducer 33 will changes relative to the tangent of the catheter's centerline 102 as the intraluminal catheter 13 is moved through a curved sheath catheter.

Figure 2B:
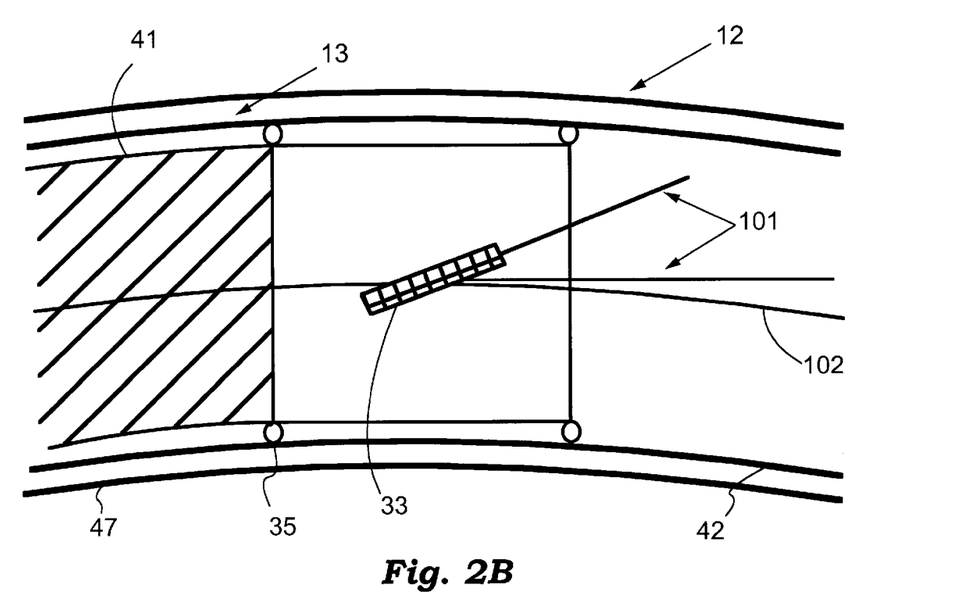

FIG. 2B shows the intraluminal catheter 13 in a sheath catheter 42 inserted into a vessel with curvature 47. The angular orientation of the ultrasound transducer 33 changes from 100, in FIG. 2, to 101, in FIG. 3. The angular orientation of the transducer is related to $v_{\parallel}$ by the following:

$$\alpha = \arcsin\left(\frac{v_{\parallel}}{v}\right)$$

Where v is the known velocity at which the intraluminal catheter moves through the sheath catheter.

Again referring to FIG. 2B, the method of this invention for measuring curvature in a vessel is to insert a flexible sheath catheter 42 into a vessel with a curvature 47 to be determined and then moving a flexible intraluminal ultrasound catheter 13 through the sheath catheter at known velocity v. The values for $v_{\parallel}$ are calculated by measuring the phase shifts of the received scattered ultrasound radiation that is converted into input electrical signals and sent to a signal processor 25 through an amplifier 31 and a filter 29 (see FIG. 1). The angular orientation α of the transducer 33 is calculated from these phase shifts and is correlated to the curvature of the vessel. There are numerous methods to derive phase shifts or time shifts of input electrical signals, all of which are known in the art. In the case where it is sufficient to detect a curvature in a vessel, the same method applies and a detection of changes in the phase shifts of input electrical signals and the input electrical signal will detect curvature.

Figure 3:
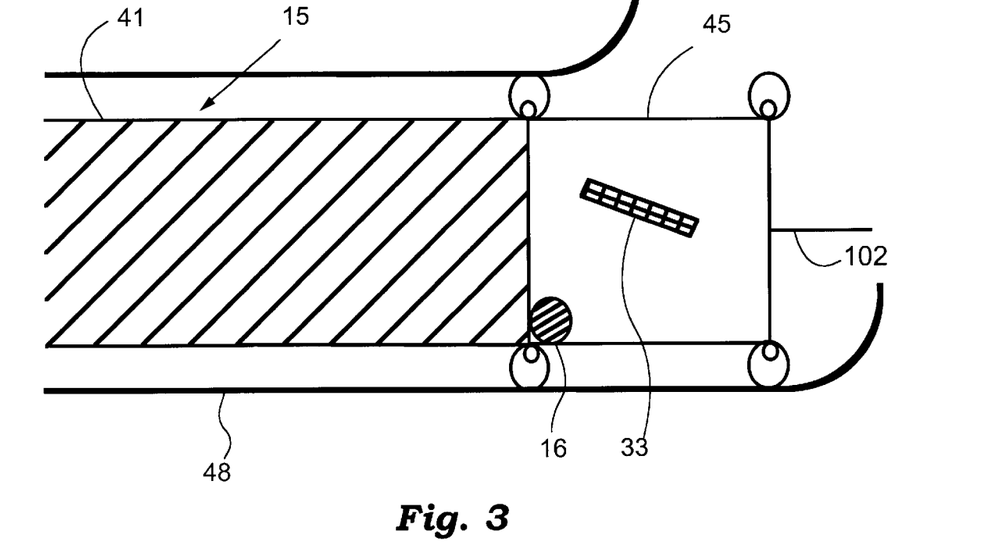
FIG. 3 is longitudinal cross sectional view an ultrasound apparatus for measuring curvature in non-biological vessels or passages.

FIG. 3 shows an ultrasound imaging apparatus that is used for detecting the curvature of a vessel where a catheter imaging apparatus is unnecessary. An ultrasound transducer 33 is mounted to a transducer supporting device 45. The transducer has an electrical connection that is connected to a signal station (not shown). The apparatus is moved through the vessel 48 by an electrical motor 16 or is moved with a cable 41 from outside of the vessel. The apparatus is moved through the vessel at a known velocity. The method described for measuring phase shifts of a plurality of input electrical signals is used to detect curvature. The apparatus is suitable for detecting the curvature in plumbing or other non-biological passages that are otherwise difficult to access.

Figure 4A:
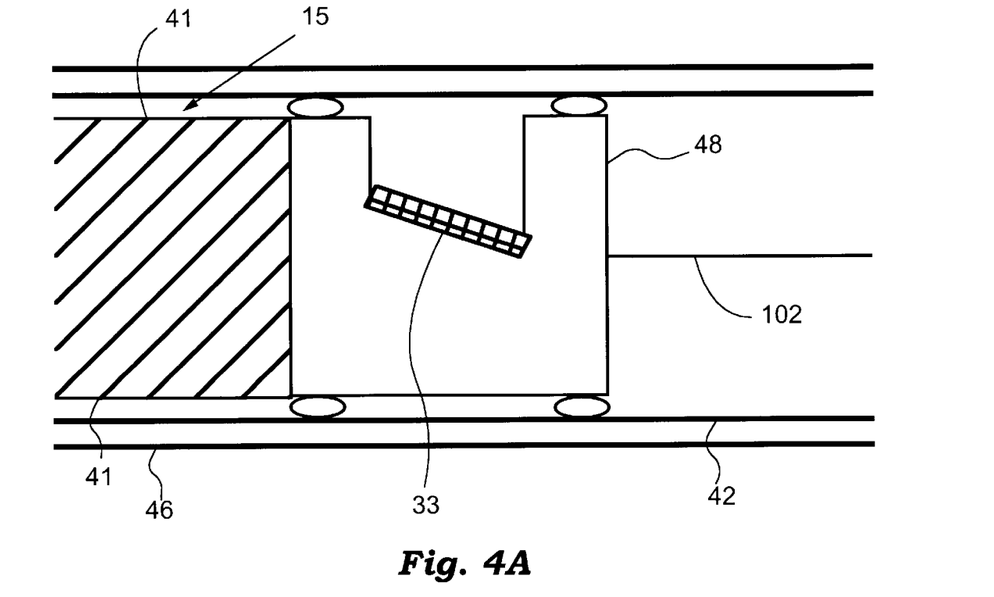
FIG. 4A is longitudinal cross sectional view an ultrasound catheter for measuring curvature in small biological vessels having a resilient deformable material between a sheath catheter and intraluminal imaging catheter.
Figure 4B:
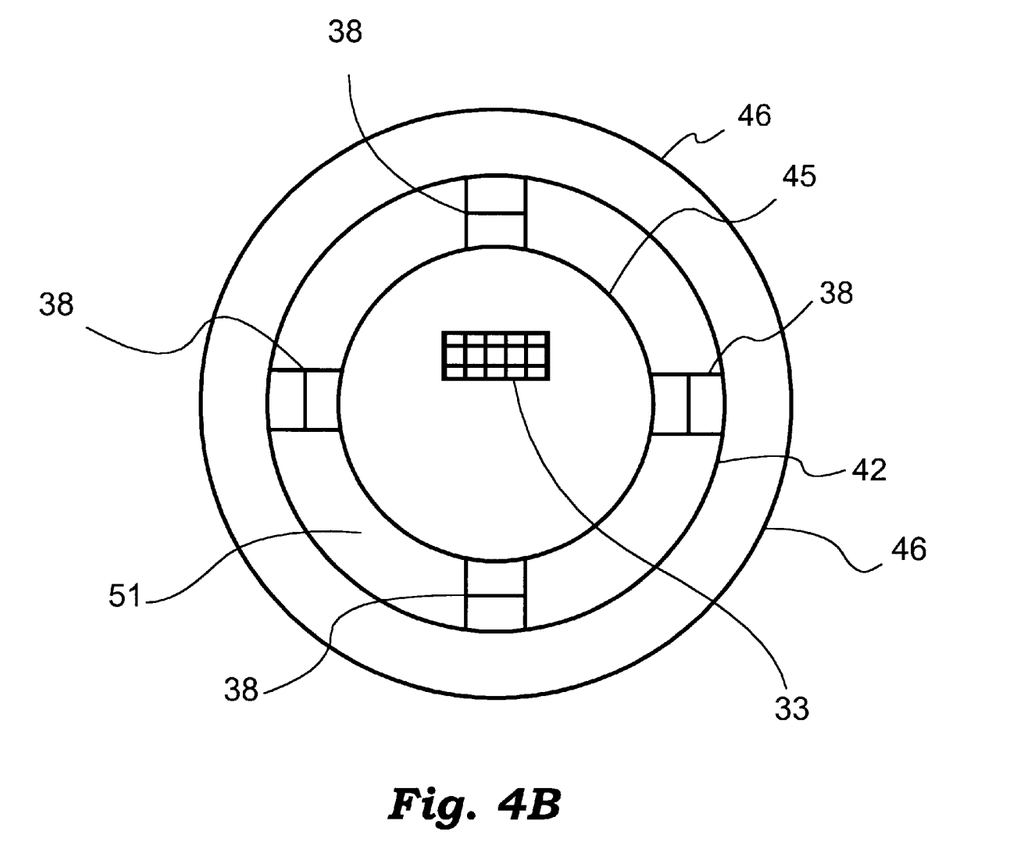
FIG. 4B is a radial cross sectional view an ultrasound catheter for measuring curvature in small biological vessels showing a resilient deformable material between a sheath catheter and intraluminal catheter.
Figure 4C:
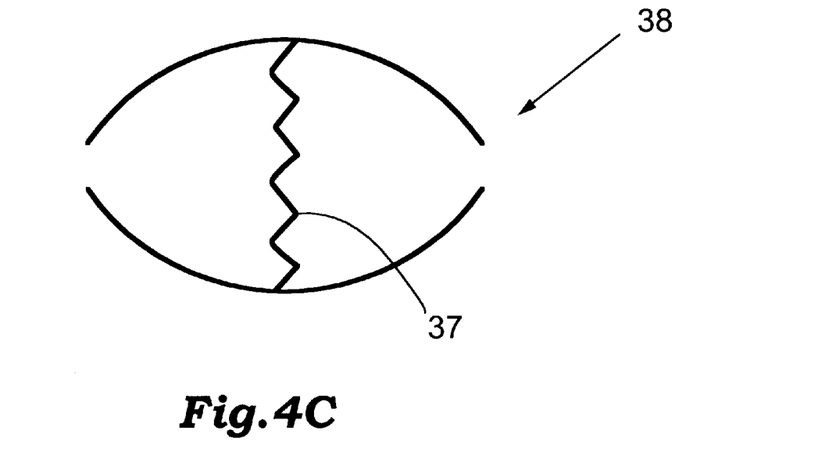
FIG. 4C is a diagram showing of leaf spring construction for a resilient deformable material used in an ultrasound imaging catheter apparatus for measuring curvature of a vessel.

FIG. 4A is a longitudinal cross-sectional view of a preferred construction for an ultrasound imaging catheter apparatus. The intraluminal catheter 15 consists of a transducer supporting device 48 with a transducer 33 mounted at an angle relative to the catheter's centerline 102. The transducer supporting device 45 is connected to a flexible cable 41. FIG. 4B shows a radial cross sectional view of the ultrasound imaging catheter apparatus. A resilient deformable material 38 is connected to transducer support device and provides a region of mobility 51 between the transducer support device 4 and the sheath catheter 42. The resilient deformable material 38 is a leaf spring. One or more leaf springs are attached to the transducer supporting device to allow the angle of the transducer to change as the transducer supporting device is moved through the curved sheath catheter. The leaf springs 38 have interior coil springs 37 (see FIG. 4C) to give the proper resiliency.

Figure 5A:
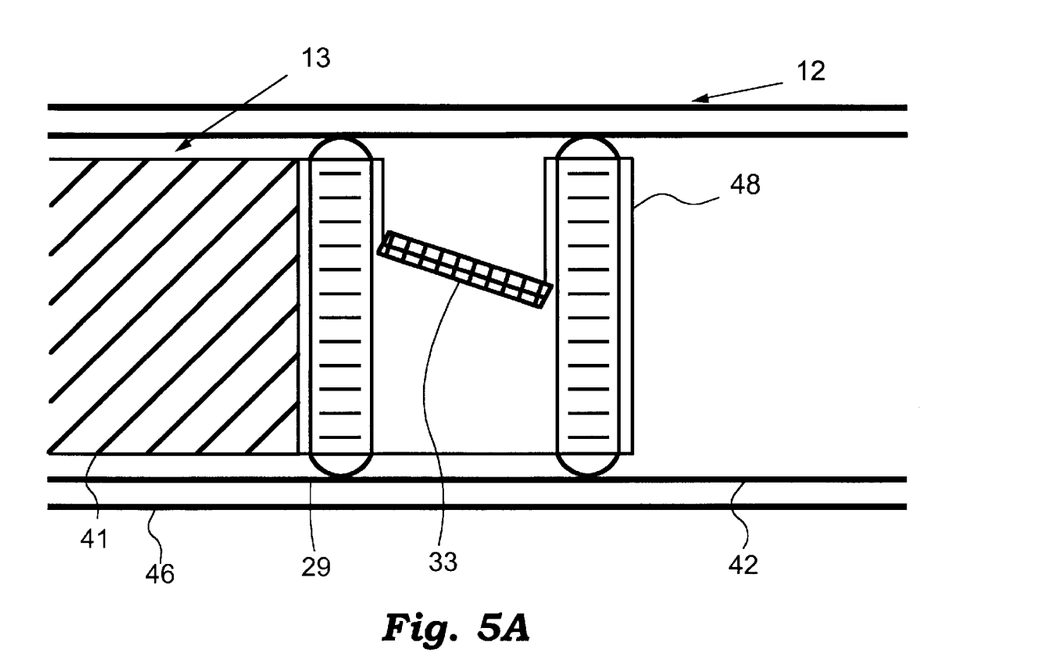
FIG. 5A is longitudinal cross sectional view an ultrasound catheter apparatus having grommet spacers as a resilient deformable material between a sheath catheter and an intraluminal catheter.
Figure 5B:
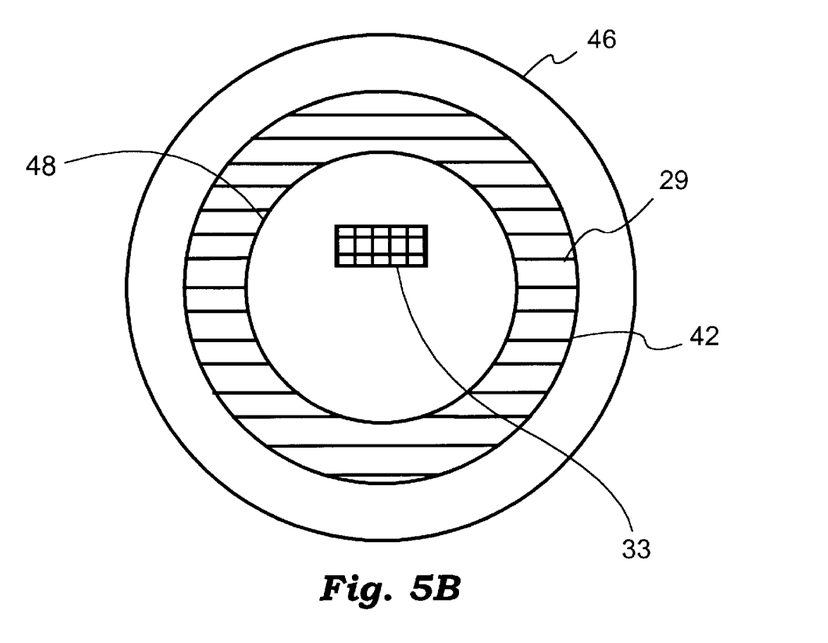
FIG. 5B is a radial cross sectional view of an ultrasound catheter apparatus for measuring curvature showing the grommet spacer encircling an intraluminal catheter.

Referring to FIG. 5A, an ultrasound imaging catheter apparatus consists of a sheath catheter 42 and intraluminal catheter 13. In this embodiment, the resilient deformable material is a rubber grommet 29 that encircles the transducer supporting device 48. FIG. 5B shows a radial cross-sectional view of the transducer supporting device 48 inside of the sheath catheter 42 with rubber grommets 29 encircling the transducer supporting device 48.

Figure 6A:
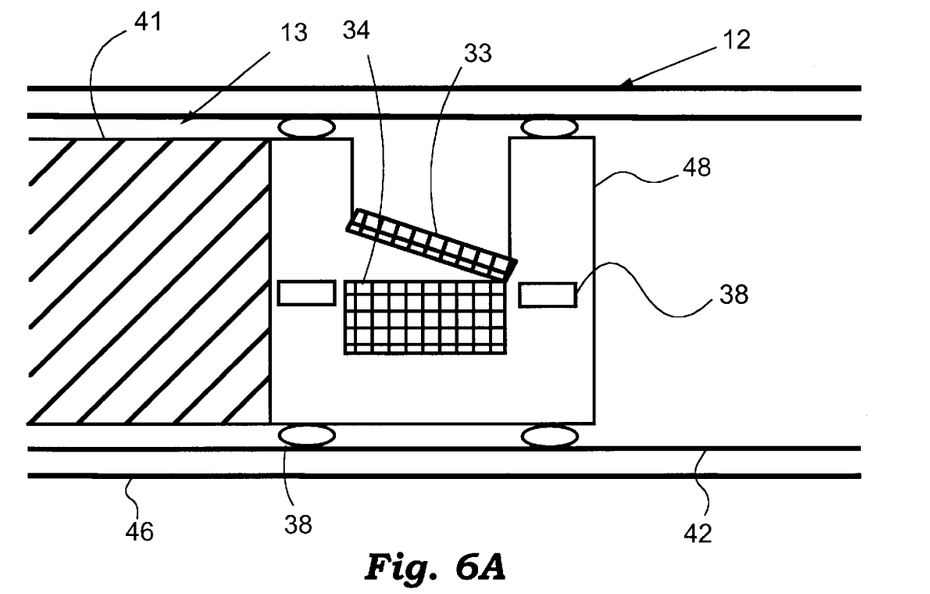
FIG. 6A is longitudinal cross sectional view an ultrasound catheter apparatus with an intraluminal catheter and two distally mounted transducers.
Figure 6B:
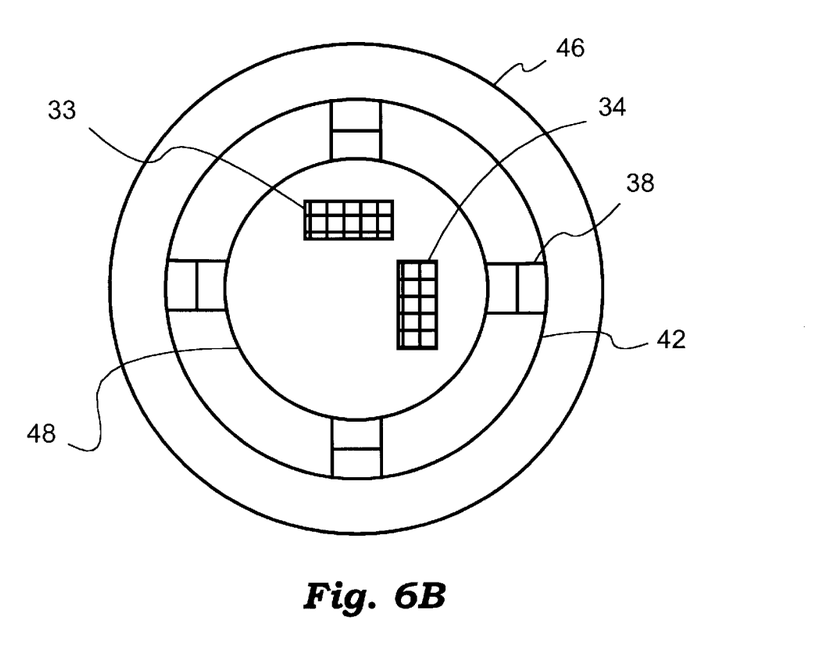
FIG. 6B is a radial cross sectional view of an ultrasound imaging catheter apparatus with an intraluminal imaging catheter and two distally mounted transducers.

Referring to FIG. 6A, an ultrasound imaging catheter apparatus comprises a flexible sheath catheter 42 and a flexible intraluminal ultrasound catheter 13 with a multiple transducers 33 and 34 mounted on a transducer support device 48. A resilient deformable material 38 is connected to the transducer support device 48 and provides for a region of separation between the sheath catheter 42 and the transducer support device 48. The resilient deformable material 38 is a spring, foam, rubber grommet or any suitable material that allows the angular orientation of the transducer supporting device and transducer to change while moving through the curved sheath catheter. FIG. 6B displays a radial cross sectional view of the imaging catheter apparatus with multiple transducer 33 and 34.

Figure 7A:
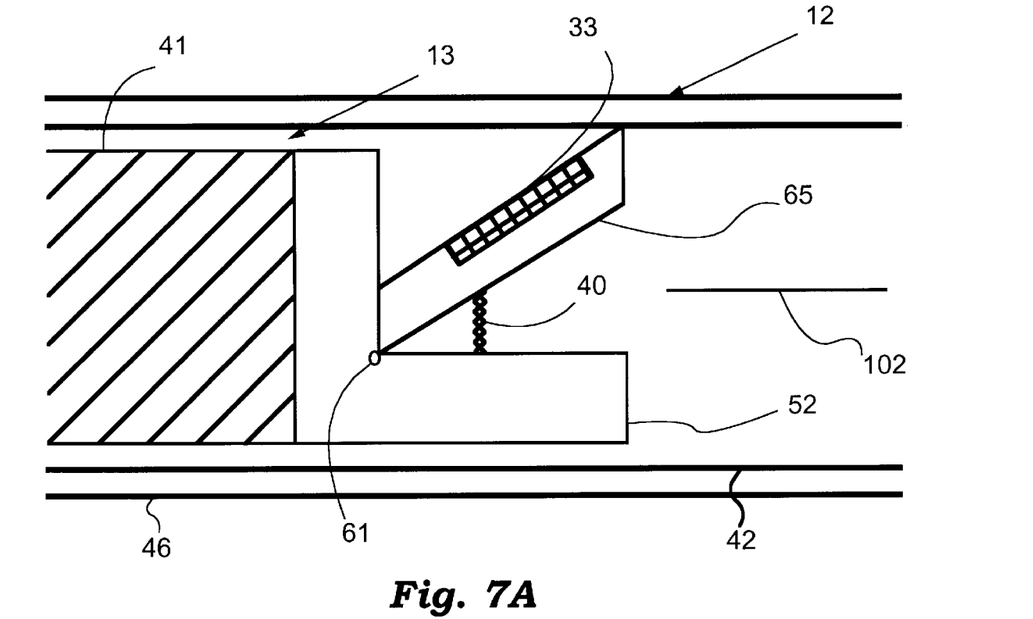
FIG. 7A is longitudinal cross sectional ultrasound catheter apparatus with a table piece mounted to and hinged to a transducer supporting device with the table piece supported by a resilient deformable material
Figure 7B:
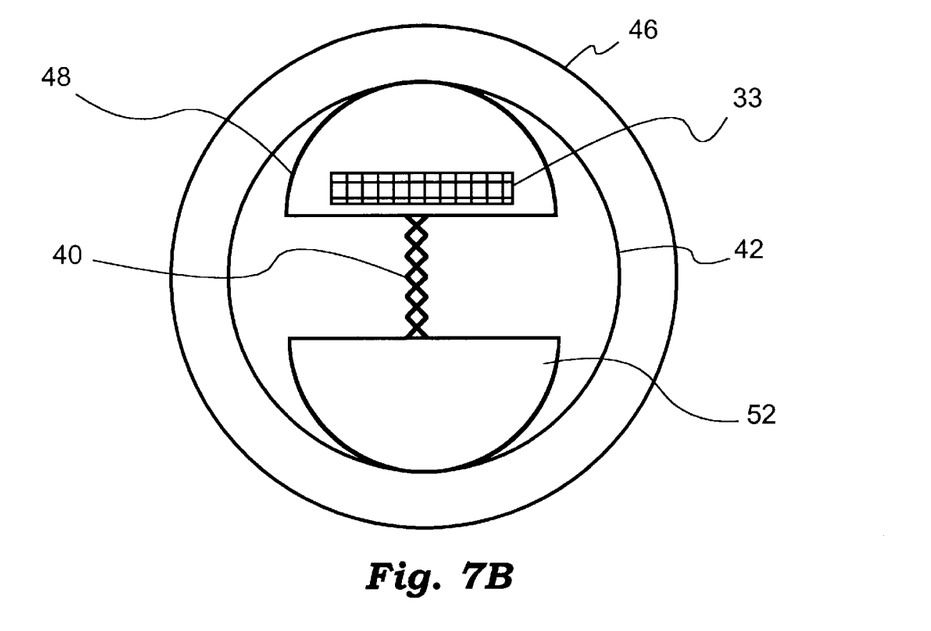
FIG. 7B is a radial cross sectional view of an ultrasound catheter apparatus with a table piece mounted to and hinged to a transducer supporting device with the table piece supported by a resilient deformable material.

Referring to FIG. 7A, the imaging catheter apparatus is comprised of a flexible sheath catheter 42 and a flexible intraluminal ultrasound catheter 13 with a supporting device 52 connected to a cable 41. A transducer 33 is mounted on a table piece 65 that is attached to the supporting device 52 by a hinge 61. The hinge 61 allows the table piece 65 to change angles with respect to tangent of sheath catheter's center-line 102 as the intraluminal catheter 13 is moved through the sheath catheter 42 with curvature. The table piece 65 is supported by a resilient deformable material 40. A resilient deformable material 40 is a spring, foam, rubber, or any material that can be deformed by force and return to it original shape when the force is removed. FIG. 7B shows a radial cross sectional view of the ultrasound imaging catheter apparatus.

The above embodiments are used to detect and measure curvature of the vessel by moving the transducer and transducer supporting device through a vessel or a sheath catheter inserted in a vessel at a known velocity. The curvature can be measured if the transducer supporting device and transducer change angular orientation with respect to the tangent of the sheath catheter's center line or the vessel's walls so that the angular orientations are dependent on the curvature of the sheath catheter or vessel.

Based on the above description, a person of ordinary skill in the art will be able to make and use the ultrasound imaging apparatus to measure the curvature of a vessel. Additionally, anyone of ordinary skill in the art will appreciate that many variations and alterations to the above details are within the scope of the invention. For example, the invention can be used in combination with conventional IVUS imaging techniques and can be applied to correct for errors that result from curvatures in the imaged vessel. Additionally, the apparatus can be modified to operate in a rotating mode and, thus, provide an apparatus for performing both conventional IVUS imaging and for measuring the curvature of vessels.

What is claimed is:

1. An apparatus for detecting a curvature in a vessel from phase shifts of a plurality of input electrical signals generated from scattered ultrasound radiation within said vessel, said apparatus comprising:

a) a signal station for generating a plurality of output electrical signals and receiving said plurality of input electrical signals;
 b) transducer support device, wherein said transducer support device is capable of translating within said vessel;
 c) a transducer for converting said plurality of output electrical signals to ultrasound radiation and converting said scattered ultrasound radiation to said input electrical signals, wherein said transducer is mounted on said transducer support device and is electrically connected to said signal station;
 d) a means for translating said transducer supporting device and said transducer at a known velocity within said vessel;
 e) a means for detecting phase shifts between said plurality of input electrical signals;
 whereby, said curvature of said vessel is detected from said phase shifts.

2. The apparatus of claim 1 wherein said means for translating said transducer support device and said transducer at a known velocity through said vessel is a flexible shaft.

3. The apparatus of claim 1 wherein said means for translating said transducer support device and said transducer at a known velocity through said vessel is a motor.

4. The apparatus of claim 1 wherein said transducer is mounted on said transducer supporting device at an angle normal to a wall of said vessel wherein said angle is greater than 0° and less than 90°.

5. An apparatus for detecting a curvature in a vessel from phase shifts of a plurality of input electrical signals generated from scattered ultrasound radiation within said vessel, said apparatus comprising:

a) a signal station for generating a plurality of output electrical signals and receiving said plurality of input electrical signals;
 b) a flexible intraluminal ultrasound catheter for insertion into said vessel said flexible intraluminal ultrasound catheter further comprising:
   i) a transducer support device said transducer support device is connected to the distal end of said intraluminal ultrasound catheter and capable of translating within said vessel;
   ii) a transducer for converting said plurality of output electrical signals to ultrasound radiation and converting said scattered ultrasound radiation to said plurality of input electrical signals said transducer is mounted on said transducer support device and is electrically connected to said signal station;
 c) a means for translating said flexible intraluminal ultrasound catheter at a known velocity within said vessel;
 d) a means for detecting phase shifts between said plurality of input electrical signals;
 whereby, said curvature of said vessel is detected from said phase shifts.

6. The apparatus of claim 5 further comprising a flexible sheath catheter for insertion into said vessel and in which said intraluminal ultrasound catheter is capable of translating through at said known velocity.

7. The apparatus of claim 5 wherein said means for translating said flexible intraluminal ultrasound catheter at a known velocity through said vessel is a flexible shaft.

8. The apparatus of claim 5 wherein said means for translating said flexible intraluminal ultrasound catheter at a known velocity through said vessel is a motor.

9. The apparatus of claim 5 wherein said transducer is mounted on said transducer supporting device at an angle normal to the surface of said sheath catheter said angle is greater than 0° and less than 90°.

10. An apparatus for measuring a curvature in a vessel from phase shifts of a plurality of input electrical signals generated from scattered ultrasound radiation 4 within said vessel, said apparatus comprising:
   a) a signal station for generating a plurality of output electrical signals and receiving said plurality of input electrical signals;
   b) a flexible intraluminal ultrasound catheter for insertion into said vessel, said flexible intraluminal ultrasound catheter further comprising:
      i) a transducer support device said transducer support device is connected to the distal end of said intraluminal ultrasound catheter and capable of translating within said a flexible sheath catheter;
      ii) a resilient deformable material said resilient deformable material connected to transducer support device and provides a region of mobility between said transducer support device and said sheath catheter;
      iii) a transducer for converting said plurality of output electrical signals to ultrasound radiation and converting said scattered ultrasound radiation to said plurality input electrical signals said transducer is mounted on said transducer support device and is electrically connected to said signal station;
   c) a means for translating said flexible intraluminal ultrasound catheter at a known velocity within said vessel;
   d) a means for measuring phase shifts between said plurality of input electrical signals;
   whereby, said curvature of said vessel is measured from said phase shifts.

11. The apparatus of claim 10 further comprising a flexible sheath catheter for insertion into said vessel and in which said intraluminal ultrasound catheter is capable of translating through at said known velocity.

12. The apparatus of claim 10 wherein said resilient deformable material is selected from the group consisting of a leaf spring, a spring, foam and a grommet.

13. The apparatus of claim 10 wherein said means for translating said intraluminal ultrasound catheter at a known velocity through said vessel is a flexible shaft.

14. The apparatus of claim 10 wherein said means for translating said intraluminal ultrasound catheter at a known velocity through said vessel is a flexible shaft.

15. A method for measuring a curvature of a vessel from phase shifts of a plurality of input electrical signals generated from scattered ultrasound radiation within said vessel, said method comprising the steps of:
   a) providing a signal station for generating a plurality of output electrical signals and receiving said plurality of input electrical signals;
   b) inserting a flexible sheath catheter into said vessel with said curvature to be determined;
   c) inserting a flexible intraluminal ultrasound catheter in said flexible sheath catheter, said flexible intraluminal ultrasound catheter having a distally mounted transducer to convert said plurality of output electrical signals to ultrasound radiation and to convert said scattered ultrasound radiation to said plurality of input electrical signals, said transducer is electrically connected to said signal station to process said plurality of input electrical signal;
   d) sending said plurality of output electrical pulses to said transducer from said signal station to produce ultrasound radiation within said flexible sheath catheter and radiating to said vessel;
   e) translating said flexible intraluminal ultrasound catheter at a known velocity within said flexible sheath catheter;
   f) receiving said scattered ultrasound radiation at said distally mounted transducer to convert said scattered ultrasound radiation to said input electrical signals;
   g) receiving said plurality of input electrical signals at said signal station to determine said phase shifts between said plurality of input electrical signals;
   h) calculating said curvature of said vessel from said phase shifts.

16. The method of claim 15 further comprising the step of translating said intraluminal ultrasound catheter in a pullback motion.

17. The method of claim 15 further comprising the step of repeating steps a) through h) to acquire multiple sets of said plurality of input electrical signals.

18. The method of 15 wherein calculation of said phase shifts of said plurality of input electrical signals is performed with a micro-processor.

19. The method of claim 15 further comprising the step of performing a 3-dimensional intravascular ultrasound imaging using said flexible intravascular ultrasound catheter.

* * * * *